(12) United States Patent
Pärssinen

(10) Patent No.: US 9,803,080 B2
(45) Date of Patent: Oct. 31, 2017

(54) ORTHOPAEDIC SPLINTING SYSTEM

(71) Applicant: Antti Pärssinen, Helsinki (FI)

(72) Inventor: Antti Pärssinen, Helsinki (FI)

(73) Assignee: ONBONE OY, Helsinki (FI)

( * ) Notice: Subject to any disclaimer, the term of this patent is extended or adjusted under 35 U.S.C. 154(b) by 213 days.

(21) Appl. No.: 14/106,973

(22) Filed: Dec. 16, 2013

(65) Prior Publication Data

US 2014/0188021 A1    Jul. 3, 2014

Related U.S. Application Data

(62) Division of application No. 13/255,936, filed as application No. PCT/FI2010/050186 on Mar. 11, 2010.

(30) Foreign Application Priority Data

Mar. 11, 2009  (FI) ..................................... 20095251

(51) Int. Cl.
*A61F 13/04*         (2006.01)
*C08L 67/04*         (2006.01)
(Continued)

(52) U.S. Cl.
CPC ............ *C08L 67/04* (2013.01); *A43B 17/003* (2013.01); *A61F 5/058* (2013.01); *A61F 5/14* (2013.01); *A61L 15/12* (2013.01); *A61L 15/125* (2013.01); *A61L 15/14* (2013.01); *C08L 97/02* (2013.01); *A63B 2071/1258* (2013.01); *A63B 2209/00* (2013.01); *C08L 2201/06* (2013.01); *C08L 2203/02* (2013.01); *Y10T 428/249921* (2015.04)

(58) Field of Classification Search
CPC combination set(s) only.
See application file for complete search history.

(56) References Cited

U.S. PATENT DOCUMENTS 3,622,431 A    11/1971   Turcksin
3,921,333 A    11/1975   Clendinning et al.
(Continued)

FOREIGN PATENT DOCUMENTS

EA    0407055 A1    1/1991
EP    0393003 A1    10/1990
(Continued)

OTHER PUBLICATIONS

Sep. 30, 2016 Search Report issued in Great Britain Application No. 1610138.8.
(Continued)

*Primary Examiner* — Ophelia A Hawthorne
(74) *Attorney, Agent, or Firm* — Oliff PLC

(57) ABSTRACT

A composite material in the form of a linear structure having a width, a length and a thickness, the composite material having a first component formed by a polymer and a second component formed by a reinforcing material, wherein the first component is a thermoplastic polymer selected from the group of biodegradable polymers and mixtures thereof, and the second component is platy wood particles. The composite material being formable at a temperature of about 50 to 70° C. and being capable of being employed as a blank for an orthopedic splint.

18 Claims, 7 Drawing Sheets

(51) Int. Cl.

| | | |
|---|---|---|
| C08L 97/02 | (2006.01) | |
| A61L 15/12 | (2006.01) | |
| A61L 15/14 | (2006.01) | |
| A61F 5/058 | (2006.01) | |
| A43B 17/00 | (2006.01) | |
| A61F 5/14 | (2006.01) | |
| A63B 71/12 | (2006.01) | |

(56) References Cited

U.S. PATENT DOCUMENTS

| | | |
|---|---|---|
| 4,019,505 A | 4/1977 | Wartman |
| 4,021,388 A | 5/1977 | Griffin |
| 4,153,051 A | 5/1979 | Shipped |
| 4,213,452 A | 7/1980 | Shipped |
| 4,240,415 A | 12/1980 | Wartman |
| 4,273,115 A | 6/1981 | Holland et al. |
| 4,376,438 A | 3/1983 | Straube et al. |
| 4,473,671 A * | 9/1984 | Green .............. A61F 13/04 523/105 |
| 4,661,535 A | 4/1987 | Borroff et al. |
| 5,417,904 A | 5/1995 | Razi et al. |
| 5,827,905 A | 10/1998 | Grigat et al. |
| 5,863,480 A | 1/1999 | Suwanda |
| 5,969,089 A | 10/1999 | Narayan et al. |
| 6,071,984 A | 6/2000 | Grigat et al. |
| 6,124,384 A | 9/2000 | Shiraishi et al. |
| 6,143,811 A | 11/2000 | Oda et al. |
| 6,184,272 B1 | 2/2001 | Foelster et al. |
| 6,479,002 B1 | 11/2002 | Becker et al. |
| 6,780,359 B1 | 8/2004 | Zehner et al. |
| 6,884,518 B2 | 4/2005 | Aho et al. |
| 6,911,522 B2 | 6/2005 | Manfredi et al. |
| 7,323,253 B2 | 1/2008 | Isaksson et al. |
| 7,601,282 B2 | 10/2009 | Gleich et al. |
| 7,988,905 B2 | 8/2011 | Hashiba et al. |
| 2001/0030031 A1 | 10/2001 | Willemse |
| 2002/0143083 A1 | 10/2002 | Komey |
| 2002/0143282 A1* | 10/2002 | Grim .............. A61F 13/04 602/5 |
| 2004/0028927 A1 | 2/2004 | Leckey et al. |
| 2005/0137304 A1 | 6/2005 | Strand et al. |
| 2006/0065993 A1 | 3/2006 | Stucky et al. |
| 2006/0241216 A1 | 10/2006 | Varachez et al. |
| 2007/0059584 A1 | 3/2007 | Nakano et al. |
| 2007/0132133 A1 | 6/2007 | Hasegawa |
| 2007/0243782 A1 | 10/2007 | Takasu et al. |
| 2007/0259584 A1 | 11/2007 | Whitehouse |
| 2007/0264460 A1 | 11/2007 | Del Tredici |
| 2007/0287795 A1 | 12/2007 | Huda et al. |
| 2008/0015285 A1 | 1/2008 | Oriani |
| 2008/0032125 A1 | 2/2008 | Terasawa et al. |
| 2008/0103423 A1 | 5/2008 | Nieberding |
| 2008/0145656 A1 | 6/2008 | Jung |
| 2008/0154164 A1* | 6/2008 | Sheehan .............. A61F 5/01 602/7 |
| 2008/0241509 A1 | 10/2008 | Lai |
| 2008/0262400 A1 | 10/2008 | Clark et al. |
| 2008/0319362 A1 | 12/2008 | Joseph |
| 2009/0036575 A1 | 2/2009 | Gardner et al. |
| 2009/0105378 A1 | 4/2009 | Mukawa et al. |
| 2009/0236766 A1 | 9/2009 | Rust et al. |
| 2010/0093890 A1 | 4/2010 | Ataka et al. |
| 2010/0136324 A1 | 6/2010 | Ohno et al. |
| 2010/0240806 A1 | 9/2010 | Kondo |
| 2011/0263762 A1 | 10/2011 | Matsuno et al. |
| 2012/0071590 A1 | 3/2012 | Parssinen |
| 2012/0090068 A1 | 4/2012 | Glass et al. |
| 2012/0090759 A1 | 4/2012 | Parssinen et al. |
| 2012/0171446 A1 | 7/2012 | Park et al. |
| 2013/0172795 A1 | 7/2013 | Parssinen |
| 2013/0225731 A1 | 8/2013 | Yin |
| 2014/0259324 A1 | 9/2014 | Behrend et al. |

FOREIGN PATENT DOCUMENTS

| | | |
|---|---|---|
| EP | 0765911 A2 | 2/1997 |
| IE | 20050593 A1 | 3/2006 |
| JP | S6158192 B2 | 12/1986 |
| JP | S6255423 B2 | 11/1987 |
| JP | H0481467 B2 | 12/1992 |
| JP | H06118460 A | 4/1994 |
| JP | H08-500748 A | 1/1996 |
| JP | H09676 A | 1/1997 |
| JP | H09-137046 A | 5/1997 |
| JP | 2-733610 B2 | 3/1998 |
| JP | 2003-165844 A | 6/2003 |
| JP | 2008-512170 A | 4/2008 |
| WO | WO9403211 * | 2/1994 |
| WO | 94/23679 A1 | 10/1994 |
| WO | 2000/035501 A1 | 6/2000 |
| WO | 2006/027763 A2 | 3/2006 |
| WO | 2007/035875 A2 | 3/2007 |
| WO | 2007/095709 A1 | 8/2007 |
| WO | 2007/095712 A1 | 8/2007 |
| WO | 2008/041215 A1 | 4/2008 |
| WO | 2008/116025 A2 | 9/2008 |
| WO | 2008/0124035 A2 | 10/2008 |
| WO | 2010/034689 A1 | 4/2010 |
| WO | 2010/103186 A2 | 9/2010 |
| WO | 2010/103187 A2 | 9/2010 |
| WO | 2012/032226 A2 | 3/2012 |
| WO | 2013/093843 A1 | 6/2013 |
| WO | 2015/059355 A1 | 4/2015 |

OTHER PUBLICATIONS

Sep. 30, 2016 Search Report issued in Great Britain Application No. 1610139.6.
Mesh to micron conversion chart, http://www.showmegold.org/news/Mesh.htm, downloaded Mar. 19, 2014.
Balatinecz, J.J., et al., "Achievements in the utilization of poplar wood—guideposts for the future," Forestry Chronicle, 2001, 77, pp. 265-269.
Chen, H.C., et al., "Effect of Wood Particle Size and Mixing Ratios of HDPE on the Properties of the Composites," Holzals Roh- under Werkstoff, 2006, 64, pp. 172-177.
Knife Ring Flakers, Pal, Technical Features. Undated.
Particle Size Conversion Table. Downloaded from the Aldrich Website on Jan. 22, 2014. Two pages.
Material safety data sheet for CAPA polycaprolactones. Perstorp. 2007.
Trademark registration record for "Lignocel." Registration date of Sep. 8, 1987. Downloaded from the USPTO website on Jan. 23, 2014.
Caufield, et al., "Wood thermaoplastic composites," "13" in: I. Rowell, M. Roger; "Handbook of wood chemistry and wood composites" Jan. 1, 2005, CRC press, XP002608 185 isbn: 084931583, pp. 365-378.
Mortain, et al., "development of new composites materials, carriers of active agents, from biodegradable polymers and wood" C.R. Chimie, vol. 7, Jun. 1, 2004, pp. 635-640, XP002608184 DOI: 10.1016/j. crci.2004.03.006.
Nov. 15, 2016 Office Action issued in European Patent Application No. 16173962.8.
Balasuriya, P.W., et al., Mechanical properties of wood flake-polyethylene composites. Part I: effects of processing methods and matrix melt flow behaviour, Composites: Part A 32 (2001) 619-629.
"CAPA for Bioplastics," Informational Slides from Perstorp, 2015.
Elias, H.G. "Plastics, General Survey," Ullmann's Encyclopedia of Industrial Chemistry, published online 2000, vol. 28, pp. 35-154.

* cited by examiner

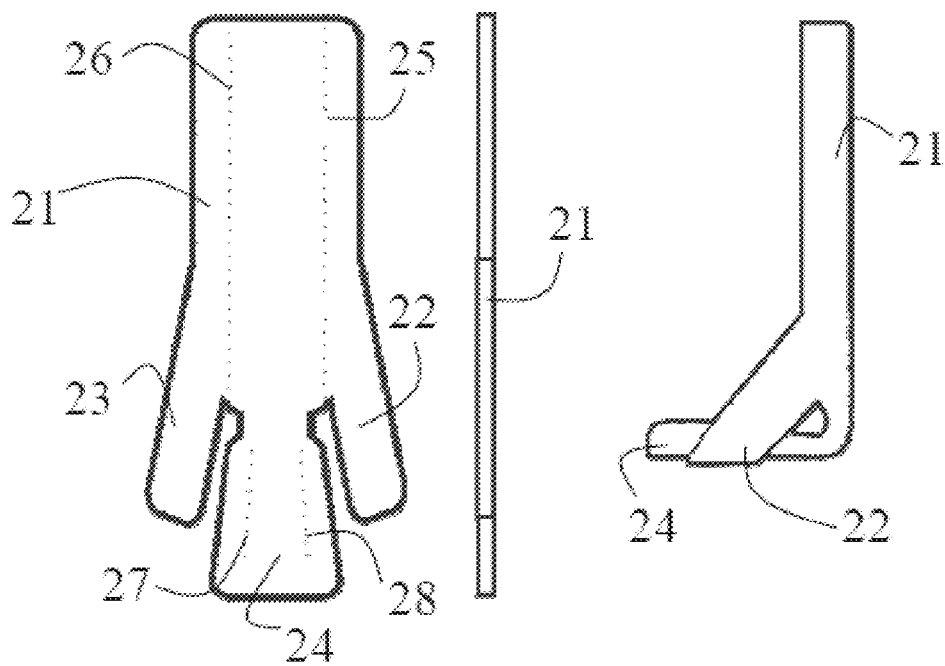
Fig. 7a　　　Fig. 7b
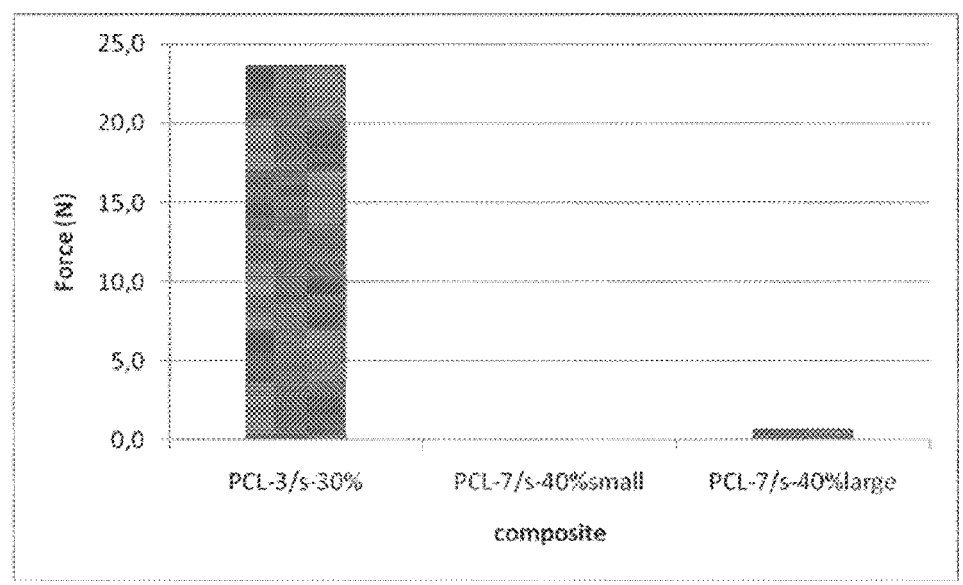
Fig. 8

ORTHOPAEDIC SPLINTING SYSTEM

BACKGROUND OF THE INVENTION

Field of Invention

The present invention relates, in general, to forming a structure on or around a body part of an animal or human being. More specifically, it relates to the field of orthopedic splinting materials, methods and apparatus. Described herein is also a method of using a novel wood-plastic composite as a splint/cast in immobilization of a fractured body part and a kit thereof.

Description of Related Art

In cases of bone fracture a splint may be applied for supporting or immobilizing a body part. Such a splint is usually wrapped with an elastic bandage and the rigid portion does not envelope the limb circumferentially. Traditional splinting techniques use a variety of materials including plaster of Paris (used first time in the Crimean war 1854 in treatment of battle wounds), fiber-glass reinforced polyurethane (DE 26 51 089), alumafoam (U.S. Pat. No. 4,213,452 and U.S. Pat. No. 4,153,051; an aluminium strip padded on one side with sponge-like foam) and complex pre-formed multilayer systems containing a plurality of straps, hooks etc. (WO 2008/041215, EP 0 393 003, EP 0 407 055).

Common to all of these techniques is that they are moldable to an extent during setup. Furthermore, depending on the applied technique the time period of mouldability followed by subsequent hardening varies greatly.

Use of the traditional splint material plaster of Paris is decreasing, despite its low costs. This is mainly due to its many well known disadvantages e.g. long setting and drying times, messy application, low strength and relative heaviness which can be quite considerable, thus limiting movement, especially of a child. Further on, during application of the plaster bandage, the user has to be extra careful for avoiding making indentations in the soft plaster that could cause local areas of high pressure leading to the formation of plaster sores. The main reason why it is still used in some casting applications is its excellent molding properties.

Fiber-glass reinforced polyurethane resin based splinting materials are considered a practical alternative for the conventional plaster of Paris casts and are currently widely used in the treatment of fractured body parts. These materials are lightweight, durable, waterproof and they tend to have a shorter setting time than traditional plaster-based materials.

Despite these advantages they are far from being ideal casting material. They require several layers for weight-bearing casts; they may crack from repetitive use and may leave sharp edges, potentially causing excoriation of the skin. The polyurethane resin based materials are quite resilient for which reason they do not conform well to the extremity. In addition, for avoiding wrinkle formation during application the extremity must be in the correct position. Further, glassfiber/polyurethane casting materials contain toxic or harmful components (cyanates and fibre-glass) and have to be applied with protective gloves. According to the MSDS of some fiber reinforced casting materials, skin contact with material during applying may cause itching, redness, dryness etc.).

Activations of the plaster-of-Paris and glassfiber/polyurethane based casting materials are based on a chemical reaction initiated with water. As a result, the hardening process of polyurethane based splints (U.S. Pat. No. 4,376,438) and of Paris (WO 00/35501) cannot be stopped or paused once the reaction has started. Therefore if there is any delay in setting of the casting application it will lead to drying of the casting material and it has to be replaced with new one. Whatever the development steps for these casting materials are they still contain toxic and irritating components, such as cyanates and calcium sulphate hemihydrates. Therefore it is very important that when a cast of the known materials is applied, all bony prominences are adequately padded for avoiding cutaneous complications.

An ongoing trend in developing alternative splinting materials is to try to use materials which are do not involve chemical reactions of toxic components and requires only heat treatment before use. One example of such a material is presented in U.S. Pat. No. 4,240,415. This material is based on electron radiated polycaprolactone. It can be heated in boiling water to give it pliable properties followed by hardening when cooling to room temperature. These types of materials are recommended for use in splints requiring revisions or functional positioning, especially in radiotherapy patient positioning and immobilization. However, they lack good molding properties and sufficient rigidity to be used in splinting of extremities.

The rigidity and usability of polymer based splinting materials have been improved by manufacturing composite materials comprising combinations of reinforcing natural fiber component and thermoplastic polymers (US 2008/0262400, US 2008/0154164, WO 94/03211, EP 0 393 003). These publications disclose polymers e.g. polycaprolactone or polyhexamethylene adipate compounded with short-fibred cellulosic additives having grain size of up to a several hundred microns are used to make up complex, preformed splinting systems. The fine particulate fillers improve the handling properties and stiffness of the formed composites. It should be pointed out that a still rather complex structure, such as a mesh of elements, with a plurality of specially designed openings and straps for fastening, is required in order to achieve an overall rigid splinting system.

It is an object of the present invention to eliminate at least a part of the problems related to conventional splinting systems and the above-mentioned problems of current products related either to their toxicity, complexity of structures or insufficient rigidity for splinting the limbs and body extremities.

SUMMARY OF THE INVENTION

An aspect of the present invention is to introduce a novel, innovative and ecologically friendly biodegradable wood-plastic composite which can be heat molded to the contours of an animal or human body part.

A further aspect of the present invention is to present a system including the novel composite material and a heating means for use in the field of orthopedics.

Further still, it is an aspect of the present invention to present a novel method for using the composite material of the present invention or the system of the present invention as a splint or cast to immobilize a body part of an animal or human.

The invention is based on the concept of providing the splint material in the form of a blank which can be shaped into the desired form of a cast or splint in situ.

The blank for an orthopedic splint is, in particular, provided in the form of a linear structure such as a plate, a sheet, a ribbon or a tape, comprising a composite material with a first component formed by a polymer and a second component formed by a reinforcing material. The polymer is a thermoplastic polymer selected from the group of biodegradable polymers and mixtures thereof, and the second component comprises a woody material derived from platy or granular wood particles. The composite material is formable at least at a temperature of about 50 to 70° C., although the temperature can be as high as 120° C. without degradation of the composite taking place.

A particular a blank for an orthopedic splint has the form of a rectangular plate having a width of 10 to 500 mm, a length of 10 to 1000 mm and a thickness of 1.5 to 10 mm, comprising 30-90 parts by weight of a polycaprolactone homopolymer having a molecular weight of about 80,000 to 200,000 g/mol and 70 to 10 parts by weight of wood granules having an average particle size of greater than 0.6 mm and up to 3.0 mm, in particular about 1 to 2.5 mm, said granules being distributed throughout the polycaprolactone homopolymer, said composite material being formable at a temperature of 50 to 120° C., in practice typically 50 to 70° C. and preferably about 65 to 70° C., and rigid at ambient temperature.

The material can be used in a method of shaping a composite material to snugly fit against a part of the body of a mammal, comprising the steps of providing the composite material in the form of an essentially rectangular, planar blank, heating the blank to a temperature in the range of 50 to 120° C., in practice typically 50 to 70° C. and preferably about 65 to 70° C., to convert the material into a manually formable state, applying the material against the target part of the body to as to make the material take up the form of the target part, and cooling the material to a temperature of less than 45° C. to make the material rigid.

The method can comprise an embodiment for forming a removable exo-skeletal device on a portion of a body of a human or animal, the method comprising the steps of;
  shaping a composite material to a desired linear form,
  heating the linearly shaped composite material in a heating device to a temperature high enough to soften the composite material yet not so high as to be harmful to skin of the human or animal,
  arranging the softened composite material on the desired portion of the body of the human or animal so that it conforms to the desired three-dimensional contoured exo-skeletal shape,
  cooling the contoured exo-skeletal composite material to a temperature approximating the ambient temperature such that the contoured exo-skeletal composite material resumes the same rigidity as the shaped linear composite material prior to heating.

More specifically, the blank according to the invention is characterized by what is stated in the characterizing part of claims 1 and 2.

The method of use is characterized by what is stated in the characterizing parts of claims 21 and 25.

The composite material of the present invention provides distinct advantages over all prior art materials used for splinting or casting an injured body part.

Thus, the present composite material is easy to work with, has a relatively light weight while maintaining the necessary structural properties of a splint/cast. It is ecologically friendly and is reusable without substantially degrading throughout uses.

A further advantage of the present invention is that the splinting system is moldable at temperatures very comfortable to patient and not scorching the skin of the patient. Furthermore, the splinting system, when solidifying, forms a rigid overall structure and does not need any further reinforcement than the natural anatomic shape to build up a reliable immobilization splint for the treatment period.

The composite material can be easily manufactured to any shape or form during manufacture or before use. However, when the splint is applied it has a three-dimensional configuration conforming to the desired body contours without undesirable wrinkling or tearing. The composite splints/casts can be cut to dimensions close to the assumed size of the treated limb from a larger blank to diminish the amount of waste material. Additionally, the leftover composite pieces as well as the abandoned and used splints/casts are fully biodegradable as their components, wood and polycaprolactone, are fully biodegradable and contain no harmful components to human or to environment.

The linear or flat composite splints, casts and blanks can be easily packaged and stored in compact piles e.g. in emergency rooms where space is limited. When composite casts are packaged appropriately they can be easily stored for at least one year.

After opening the cast package, the wood like composite plate can be handled without any protection, e.g. gloves and masks, since the component materials are non-toxic. The composite can then be placed in to a heating device having an adjustable thermostat system or a preprogrammed thermostat tailored to the system. The cast can be heated to operating temperature of around 65° C., preferably in dry condition, in less than 10 minutes. At this temperature, the composite is soft, pliable and can be applied to the desired body part or region. Due to thermal characteristics of wood or woody components, the cast does not feel hot on a skin of operating personnel or a patient. The created form closely matches the anatomical contours of the patient's body parts without undesired wrinkling or tearing.

Due to unique properties of splinting system, the cast remains applicable for around 5-10 minutes after heating even if the surface temperature of the cast decreases close to body temperature. This unique formability and time slot is due to appropriate crystallinity of polymer matrix and wood or woody components providing thermal insulation of certain degree. During the application time, the cast can be easily cut with conventional scissors and reshape to accurately match an injured body part. The full strength properties of the cast is achieved approximately in 20 minutes after the initial hardening; however the time may be shortened to few minutes when an external cooling system is used. In case the clinical practitioner needs to re-formulate the shape of the splint, it can be re-heated to the operating temperature. In this way, an unlimited working period can achieved, which is a clear advantage over the current chemically curable plastic or chalk (POP) splints. It is also a distinctive property of the novel splinting system that notwithstanding the cast is moldable during its cooling period down to lower surface temperatures, the hardened splint does not yield or become malleable until the original operating temperature for the splint is again reached.

The entire treatment system is water-free and during heating, applying and use there are no dust, chemicals or vapors released.

In contrast to the materials in the prior art, the casting material of an aspect of the present invention neither contains a mesh type of structure, nor layers of different materials. The casting material is thoroughly uniform, homogeneous and no "weak spots" in its mechanical strength of the three-dimensional configuration are observed.

The present invention will now be described in more detail with the aid of the detailed description of the preferred embodiments.

BRIEF DESCRIPTION OF THE DRAWINGS

FIG. 7a shows the front and side views of an unfolded anatomic ankle cast of the kind depicted in FIG. 6, and FIG. 7b shows the side view of the same cast in folded position; and (example 5)

FIG. 8 is a bar chart showing the results of tests carried out with a peel adhesion test method (Example 6).

DETAILED DESCRIPTION OF PREFERRED EMBODIMENTS

Figure 1:
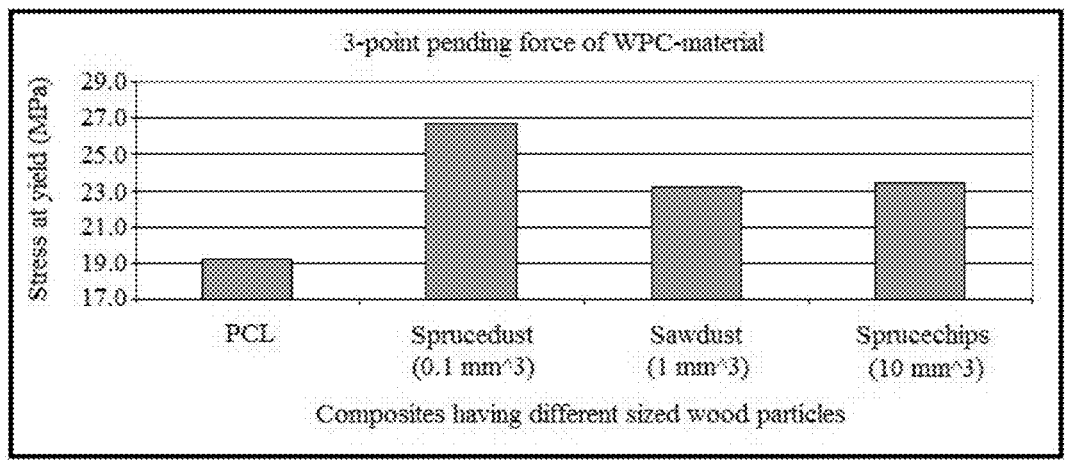
FIG. 1 is a bar chart showing the stress force of test sample in 3-point bending test of wood-PCL composites (PCL quality=PCL-3).

An aspect of the present invention is the presentation of a novel composite material. The material is novel in at least its composition and in its properties. The novel composite material is presented as being formed in to a blank, to be sized prior to application, or formed in to desired specific shapes during manufacture. In addition to the novel composite material in itself, there is provided a kit comprising at least one or more forms of the composite material and a heating means to prepare the composite material for application.

The composite retains its shape as it cools down. It is substantially rigid but flexible so as to be supportive and comfortable. Rigidity is generally achieved when a sample heated to the above indicated softening temperature is cooled to below 50° C., in particular to less than 45° C., preferably less than 40° C. Typically, the composite is rigid at ambient temperature, a suitable temperature of use is about 20 to 50° C., in particular 22 to 40° C.

As evident from the above, the material of the present invention can be simply manufactured by mixing the first component, i.e. a suitable polymer material for example in the form of pellets, with the second component i.e. wood particles or granules, by melt mixing. The mixing can be carried out in any conventional apparatus designated for melt mixing or melt processing. One example is a heatable vessel having a mechanical stirrer.

The uniformity of the composite can be increased by using an extruder, kneader or any device suitable for mixing thermoplastic polymers.

By using an extruder mixing apparatus equipped for example with two hoppers, each containing one of the components of the material, the desired amount of each component can be fed in to the mixing chamber of the apparatus. Then, by way of the mixing means in the mixing apparatus, there is formed a homogeneous mixture of the first and second components prior to the formation of the formation of the material.

One advantage to the material being formed by such a homogeneous mixture of the components is that the forces necessary to form a substantially homogeneous material are reduced. Therefore, little or no compression force is necessary to facilitate mixing of the components in a material formation step. The importance of this factor is that, by way of the homogeneous mixture, larger particles of each component can be used which would otherwise have been destroyed when subjected to high compression forces.

The material can be applied for use after it has been recovered from the mixing device and formed into desired shape for example into a sheet or plate or roll or any similar planar, folded, bent or tubular structure, but the material can even be formed directly on the patient.

The material mixed with an extruder can be shaped with appropriate nozzle to the shape of e.g. rectangular sheet or plate which can be used directly after cutting e.g. as a finger splint.

The desired profile for the splints can be manufactured with the extruder manufactured sheet or plate with e.g. laser cutting, water jet cutting, eccentric pressing or with any tool capable for producing regular shape profiles. The present material can also be process with compression moulding, injection moulding, die-casting, and pressure die-casting.

The sheet or plate can have a thickness of, generally about 1 to 50 mm, in particular about 1.5 to 30 mm, for example 1.5 to 20 mm. A typical thickness is about 2 to 6 mm. The length and the width of the sheet or plate can vary in the range of about 1 to 150 cm (length) and 1 to 50 cm (width), a typical length being about 10 to 60 cm and a typical width being about 5 to 20 cm.

The proportions between the components of the material can vary in a broad range. Thus, generally, 5 to 99 wt-%, for example 40 to 99 wt-%, of the material is formed by the thermoplastic polymer component and 1 to 95 wt-%, for example 1 to 60 wt-%, by the woody material.

The weight ratio of polymer-to-wood can easily be modified and the weight percent of wood, based on the total weight/volume of the composition, may vary between 1 and 70%, preferably however in the range of 10 to 60 weight percent, or 20 to 60 weight percent, and 15 to 50%, or 25 to 50%, by volume.

The second component comprises or consists essentially of a woody material having a smallest diameter of greater than 0.1 mm. As will be discussed below, there can also be other wood particles present in the second component. The woody material can be granular or platy. According to one embodiment, the second component comprises a woody material derived from platy wood particles having a smallest diameter of greater than 0.1 mm.

Thus, generally, the wood component can be characterized generally as being greater in size than powder.

The size and the shape of the wood particles may be regular or irregular. Typically, the particles have an average size (of the smallest dimension) in excess of 0.1 mm, advantageously in excess of 0.5 mm, for example in excess of 0.6 mm, suitably about 1 to 40 mm, in particular about 1.2 to 20 mm, preferably about 1.5 to 10 mm, for example about 1.5 to 7 mm. The length of the particles (longest dimension of the particles) can vary from a value of greater than 1 mm to value of about 1.8 to 200 mm, for example 3 to 21 mm.

The woody particles can be granular, platy or a mixture of both. Woody particles considered to be granular have a cubic shape whose ratio of general dimensions are on the order of thickness:width:length=1:1:1. In practice it is difficult to measure each individual particle to determine if it is a perfect cube. Therefore, in practice, particles considered to be granular are those where one dimension is not substantially different than the other two.

Woody particles considered to be platy means that they have generally a plate-shaped character, although particles of other forms are often included in the material. The ratio of the thickness of the plate to the smaller of the width or length of the plate's edges is generally 1:1 to 1:500, in particular about 1:2 to 1:50. Preferably, the woody particles include at least 10% by weight of chip-like particles, in which the ratio of general dimension are on the order of thickness:width:length=1:1-20:1-100, with at least one of the dimension being substantially different than another.

Based on the above, the platy particles of the present invention generally comprise wood particles having at least two dimensions greater than 1 mm and one greater than 0.1 mm, the average volume of the wood particles being generally at least 0.1 mm$^3$ more specifically at least 1 mm$^3$.

"Derived from platy wood particles" designates that the wood particles may have undergone some modification during the processing of the composition. For example, if blending of the first and second components is carried out with a mechanical melt processor, some of the original platy wood particles may be deformed to an extent.

The majority of wood particles greater in size than powder, which particles may be granular or platy, typically make up more than 70% of the woody material.

The wood species can be freely selected from deciduous and coniferous wood species alike: beech, birch, alder, aspen, poplar, oak, cedar, *Eucalyptus*, mixed tropical hardwood, pine, spruce and larch tree for example.

Other suitable raw-materials can be used, and the woody material of the composite can also be any manufactured wood product.

The particles can be derived from wood raw-material typically by cutting or chipping of the raw-material. Wood chips of deciduous or coniferous wood species are preferred.

As mentioned above, in WO 94/03211 a composite material is described, based upon polycaprolactone, ground almond shell and wood flour. The known material is impaired by several disadvantages, such as a high density of 1.1 kg/m$^3$ or even more, as a result of the small particle sizes of the filler material [wood, less than 600 microns (600 μm)]. Another disadvantage related to the use of small particle sized fillers, is the poor adhesive properties of composite material. According to our experiments (cf. Example 10 below), composites consisting of 40 weight percentage of wood dust sized between 0-800 microns reveal zero adhesion toward bandage material (compression force of 0.1 bars).

To avoid mobilization of the splint and to improve immobilization of the fractured limb during setting of the bandages minor adhesion forces are required. Further on, polycaprolactone polymer (CAPA 656) presented in examples of WO 94/03211 has too low viscosity (melt flow index value of 7 g/10 minutes with 2.16 kg standard die at 160° C.) to be used at practical applying temperature of 65° C. The composite manufactured of PCL having MFI value of seven (PCL-7) tears too easily and does not tolerate strong bending during applying.

By contrast, the present composite materials provide excellent properties also in this respect.

In addition to wood chips and other platy particles, the present composition can contain reinforcing fibrous material, for example cellulose fibers, such as flax or seed fibers of cotton, wood skin, leaf or bark fibers of jute, hemp, soybean, banana or coconut, stalk fibers (straws) of hey, rice, barley and other crops and plants including plants having hollow stem which belong to main class of Tracheobionta and e.g. the subclass of meadow grasses (bamboo, reed, scouring rush, wild angelica and grass).

Furthermore, the composition may contain particulate or powdered material, such as sawdust, typically having particles with a size of less than 0.5 mm*0.5 mm*0.5 mm. Particulate or powdered material is characterised typically as material of a size in which the naked eye can no longer distinguish unique sides of the particle. Platy particles are easily recognizable as one dimension is recognizable by the naked eye as being larger than another. Granular particles, while having substantially equal dimensions, are of such dimension that their unique sides can be determined by the naked eye and oriented.

More particularly, particulate or powdered materials are of such a small or fine size that they cannot be easily oriented with respect to their neighbours. Granular and platy particles are of such as size that their sides are recognizable and orientatable.

The desired composition of the second component can be achieved by sifting woody particles through one or more meshes having one or more varying qualities. The desired composition can also be accomplished by other well known techniques in the art for sorting and separating particles in to desired categories. The desired composition may be the resultant composition of one sifting or separating process. The desired composition may also be a mixture of resultant compositions from several sifting or separation processes.

A particularly interesting raw-material comprises wood particles, chips or granules, of any of the above mentioned wood species having a screened size of greater than 0.6 mm and up to 3.0 mm, in particular about 1 to 2.5 mm on an average.

According to one embodiment, the weight ratio of fibrous material (optionally including said powdered material) to the platy material (dry weight) is about 1:100 to 100:1, preferably about 5:100 to 50:50. In particular, the woody material derived from the platy wood particles forms at least 10%, preferably about 20 to 100%, in particular about 30 to 100%, of the total weight of the second component.

The woody material makes up at least and preferably more than 70% of the second component.

In addition to wood-based powdered materials, inorganic particulates or powdered materials such as mica, silica, silica gel, calcium carbonate and other calcium salts such as tricalcium orthophosphate, carbon, clays and kaolin may be present or added.

According to an alternative, a composite useful as an orthopedic material, comprises a first component formed by a polymer and a second component formed by a reinforcing material, wherein the first component comprises a thermoplastic polymer selected from the group of biodegradable polymers and mixtures thereof, and the second component comprises reinforcing fibres. Such fibers can be selected from the group for example of cellulose fibers, such as flax or seed fibers of cotton, wood skin, leaf or bark fibers of jute, hemp, soybean, banana or coconut, stalk fibers (straws) of hey, rice, barley and other crops including bamboo and grass. According to an interesting embodiment, the wood filler may consist of or consist essentially of fibres of the indicated kind. The polymer component can be any of the below listed polymers, caprolactone homo- or copolymers having a molecular weight of about 60000 g/mol up to 250,000 g/mol being particularly preferred.

The thermoplastic polymer and its properties will be discussed in more detail below, but for the sake of order it is pointed out that in all of the above mentioned embodiments, wherein various fillers are used as a second and a third and even fourth component of the composition, substantial advantages with respect to biodegradability and mechanical properties have been found using caprolactone polymers, in particular homopolymers, as thermoplastics. The particularly preferred polymer component is a caprolactone homopolymers having a molecular weight of above 80,000 g/mol. Specifically, caprolactone having a molecular weight of between 100,000 g/mol and 200,000 g/mol as been found to be advantageous both in terms of resultant properties and cost.

Before the woody particles are mixed with the thermoplastic polymer they can be surface treated, e.g. sized, with agents which modify their properties of hydrophobicity/-hydrophobicity and surface tension. Such agents may introduce functional groups on the surface of the granules to provide for covalent bonding to the matrix. Even increased hydrogen bonding or bonding due to van der Waals forces is of interest. The woody particles can also be surface treated with polymer e.g. PCL having low viscosity and molar mass values to increase holding powers between wood and PCL having high viscosity value.

The wood material can be also coated or treated with anti-rot compound e.g. vegetable oil to improve its properties against aging and impurities.

The wood material can be dehydrated to make it lighter before mixing it with polymer. The mechanical and chemical properties of wood material can be improved with heat treatment, which is known to decrease e.g. swelling and shrinkage.

In the composition according to an aspect of the present invention, the first component (the polymer) forms the matrix of the composite, whereas the microstructure of the second component in the composition in discontinuous. The particles of the second component can have random orientation or they can be arranged in a desired orientation. The desired orientation may be a predetermined orientation.

As mentioned above, according to a preferred embodiment, a polycaprolactone polymer (in the following also abbreviated "PCL") is used as a thermoplastic polymer in the first component of the composition. The polycaprolactone polymer is formed by repeating units derived from epsilon caprolactone monomers. The polymer may be a copolymer containing repeating units derived from other monomers, such as lactic acid, glycolic acid, but preferably the polymer contains at least 80% by volume of epsilon caprolactone monomers, in particular at least 90% by volume and in particular about 95 to 100% epsilon caprolactone monomers.

In a preferred embodiment, the thermoplastic polymer is selected from the group of epsilon-caprolactone homopolymers, blends of epsilon-caprolactone homopolymers and other biodegradable thermoplastic homopolymers, with 5-99 wt %, in particular 40 to 99 wt %, of an epsilon-caprolactone homopolymer and 1-95 wt %, in particular 1 to 60 wt %, of a biodegrable thermoplastic polymer, and copolymers or block-copolymers of epsilon-caprolactone homopolymer and any thermoplastic biodegradable polymer, with 5 to 99 wt %, in particular 40 to 99 wt % of repeating units derived from epsilon-caprolactone and 1 to 95 wt %, in particular 1 to 60 wt %, repeating units derived from other polymerizable material.

Examples of other biodegradable thermoplastic polymers include polylactides, poly(lactic acid), polyglycolides as well as copolymers of lactic acid and glycolic acid.

The first polymer component, in particular the epsilon caprolactone homo- or copolymer, has an average molecular weight of 60,000 to 500,000 g/mol, for example 65,000 to 300,000 /mol, in particular at least 80,000 g/mol, preferably higher than 80,000 and up to 250,000.

The molding properties of the present invention can be determined by the average molecular weight ($M_n$) of the polymer, such as epsilon caprolactone homo- or copolymer. A particularly preferred molecular weight range for the $M_n$ value of PCL is from about 100,000 to about 200,000 g/mol.

The number average molar mass (Mn) and the weight average molar mass (Mw) as well as the polydispersity (PDI) were measured by gel permeation chromatography. Samples for GPC measurements were taken directly from the polymerization reactor and dissolved in tetrahydrofuran (THF). The GPC was equipped with a Waters column set styragel HR(1,2 and 4) and a Waters 2410 Refractive Index Detector. THF was used as eluent with a flow rate of 0.80 ml/min at a column temperature of 35° C. A conventional polystyrene calibration was used. In determination of the water content of the monomer at different temperatures a Metroohm 756 KF Coulometer was used.

The properties of moldability of the present composition can also be determined by the viscosity value of the polymer. For an epsilon caprolactone homopolymer: when the inherent viscosity (IV)-value of PCL is less than 1 dl/g the composite is sticky, flows while formed and forms undesired wrinkles while cooling. When PCL having IV-value closer to 2 dl/g is used the composite maintains its geometry during molding on the patient and it may be handled without adhesive properties. Thus, IV values in excess of 1 dl/g are preferred, values in excess to 1.2 dl/g are preferred and values in excess of 1.3 dl/g are particularly suitable. Advantageously the values are in the range of about 1.5 to 2.5 dl/g, for example 1.6 to 2.1 dl/g. Inherent Viscosity values were determined by LAUDA PVS 2.55d rheometer at 25° C. The samples were prepared by solvating 1 mg of PCL in 1 ml chloroform ($CH_3Cl$).

A particularly important feature of the thermoplastic polymer is the viscosity which is relatively high, typically at least 1,800 Pas at 70° C., 1/10 s; the present examples show that the viscosity can be on the order of 8,000 to 13,000 Pas at 70° C., 1/10 s (dynamic viscosity, measured from melt phase). Below the indicated value, a reinforced material readily wrinkles during forming it on a patient.

The thermoplastic material is preferably a biodegradable polymer (only) but also non-biodegradable polymers may be utilized. Examples of such polymers include polyolefins, e.g. polyethylene, polypropylene, and polyesters, e.g. poly(ethylene terephthalate) and poly(butylenes terephthalate) and polyamides. Combinations of the above biodegradable polymers and said non-biodegradable polymers can also be used. Generally, the weight ratio of biodegradable polymer to any non-biodegradable polymer is 100:1 to 1:100, preferably 50:50 to 100:1 and in particular 75:25 to 100:1. Preferably, the composite material has biodegradable properties greater, the material biodegrades quicker or more completely, than the thermoplastic material alone.

According to the invention, a polymer of the afore-said kind is preferably moldable at a temperature as low as +50° C., in particular at +65° C. or slightly above, and it can be mixed with wood particles or generally any porous material gaining increased rigidity of the formed composite. The polymer component, such as polycaprolactone homopolymer, defines the form of the splinting material against the skin.

The modulus (Specific Young's modulus), at ambient temperature, of the polymer component is greater than 300 MPa. By compounding the polymer with the wood component, the modulus will be improved (cf. below), typically it is about 350 to 2000 MPa for the composition.

The present material contains a significant portion of wood granules having a particle size greater than the micrometer range, for example a size of about 0.75 mm to 50 mm. When the material is shaped into a sheet, (at least most of) the wood granules become oriented in two dimensions within forming of the thermoplastic material into sheets.

According to a preferred embodiment, the present method of producing a composite useful as an orthopedic material comprises the steps of
  mixing together 10 to 100 parts, preferably 50 to 100 parts, by weight of a first component formed by a polymer selected from the group of biodegradable polymers and mixtures thereof, and
  1 to 100 parts, preferably 10 to 50 parts, by weight of a second component formed by a reinforcing material, present in the form of platy wood particles.

The mixing can be melt mixing carried out at a temperature sufficient for melting the thermoplastic polymer, e.g. at about 50 to 150° C.

The molten polymer mass containing a mixture of biopolymer and reinforcing platy or granular particles can be shaped manually or, according to a preferred embodiment by moulding in a mould.

The molten polymer mass can be subjected to tensile forces to achieve a desired orientation of the polymer and, in particular, the reinforcing particles.

The manufacturing process can, on an industrial scale, be carried out as follows:

In a first step wood chips or granules and plastic granules are mixed to form a uniform blend before pouring into the feed hopper of an extruder. The mixing process can be carried out also by feeding of the virgin materials to the extruder directly by using separate feeding hoppers.

The compounding is then carried out in, e.g., an extruder, in particular a single screw extruder. In the compounding process the screw extruder profile of the screw is preferably such that its dimensions will allow relatively large wood chips to move along the screw without crushing them. Thus, the channel width and flight depth are selected so that the formation of excessive local pressure increases, potentially causing crushing of the wood particles, are avoided. The temperature of the cylinder and the screw rotation speed are also selected such as to avoid decomposition of wood chip structure by excessively high pressure during extrusion. For example a suitable barrel temperature can be in the range of about 110 to 150° C. from hopper to die, while the screw rotation speed was between 25-50 rpm. These are, naturally, only indicative data and the exact settings will depend on the actual apparatus used.

The compounded composite material obtained from the melt processing/compounding step is then profiled in the tool to a homogeneous product, e.g. a sheet or plate, for example using suitable mechanical processing. One particularly suitable method is calendaring. Another suitable process is by pressing.

To avoid changes in the structure of the wood material during mechanical processing, the composite material can be subjected to gentle folded between the processing steps. Usually, the mechanical processing is carried out at a temperature well above the glass transition/melting point of the polymer.

The density of composite manufactured typically lies in the range of about 600 to 850 kg/m$^3$, depending on the weight percent of wood in material.

The manufacturing process is described in more detail in our co-pending patent application titled "Method of Producing a Composite Material", the content of which is herewith incorporated by reference.

The reinforced material typically exhibits properties selected from one or several of the following:
  a density of the composition is at least 5% less than that of the polymer component (e.g. epsilon-caprolactone homopolymer) as such;
  a Specific Young's modulus value in 3-bending test of the composition is at least 10% higher than that of the polymer component (e.g. epsilon-caprolactone homopolymer) as such; and
  a thermal conductivity on the order of about 0.5 W/m·K, at the most.

At a manipulation temperature of 50 to 70° C., typically about +65° C. or slightly more, the splinting material can be manipulated and manually shaped for up to 10 minutes and it is typically pliable for 3-10 minutes after the finishing of heating, depending of the size of splint. The material hardens entirely in one hour. Operation time of the melt material can be expanded by heating the material close to +100° C., which is the temperature limit for the material to be handled without protective gloves. The material can be heated to +150° C. and held there for several hours without changes in the material properties.

To achieve rapid solidification of the material, a cooling spray or a cooling gel or wrap can be used.

As mentioned above, and as will be discussed below in connection with the examples, the present composition can be used as a composite material according to any of the preceding claims for use as an orthopedic material. Such materials are exemplified by finger splints, wrist casts and ankle casts. Generally, the platy particles form about 30 to 70%, preferably in excess of 40 up to about 60%, of the total weight of the composition, for finger splints and for ankle casts about 20 to 60%, preferably about 30 to 50% of the total weight of the composition. There is typically a greater portion of the larger particles present in the larger casts which will reduce the total weight of the cast without impairing the strength properties thereof.

Properties of the Novel Composite Material

The composite cast/splint is very user-friendly. There is no unpleasant odor from volatile chemicals, quite the opposite; there is only mild odor of virgin wood e.g. spruce and aspen. Also the appearance of the casting material is trustworthy. The polymer material is not visible and the whole look is based on small wood particles.

Important from a usage point of view of the composite is the time that it will stay pliable and applicable after heating procedure is terminated. Further on, essential is also to find out how long it will take for the composite to set and harden fully. Apparent problem to the evaluation of hardening time of the composite splint is that temperature of the patient skin and surroundings which both may vary greatly. At the coldest skin temperatures may be slightly below 20° C. and at the hottest close to the body temperatures of 37° C. At RT (22-24° C.) average skin temperatures are between 30 and 34. To gain these time windows for setting and hardening some experiments were carried out. The test specimen was cooled down to the ambient temperature of ~22° C. and to the skin temperature of 31° C. after heating was ended. Specimens were placed onto materials having different thermal conductivities.

The cooling of the composite when placed onto the platform having low thermal conductivity represents the situation when the splint has long time to reach equilibrium temperature at RT. Based on the results the cooling process can be divided into three phases. 1) Rapid cooling phase when the temperature of test sample decreases from starting temperature of ~65° C. to 38° C. during 5 minutes. 2) Steady state phase during the temperature of test specimen remains at 38° C. for 5 minutes. 3) Slow cooling phase during the temperature of the test specimen slowly approaches the equilibrium temperature of surroundings during 50 minutes.

The cooling of the composite when placed directly onto the skin of the thigh represents the situation when the splint has shortest possible time to reach equilibrium temperature at limb temperature of ~31° C. when no additional cooling is utilized (e.g. cooling spray). In general, the temperature behavior of the test specimen is similar with data presented in the previous experiment. The differences in cooling process are at the Rapid cooling phase and at the Slow cooling phase. The temperature of the test specimen decreases from ~67° C. to 38° C. during 3 minutes at the first phase. 2) Steady state phase at 39° C. lasts for 5 minutes. 3) Slow cooling phase during the temperature of the test specimen slowly approaches the equilibrium temperature of surroundings during 30 minutes.

The pliability of the test specimen was tested manually by lifting one side of sample and allowing it to settle down. After the settling procedure of the sample plate was not anymore complete the pliability is lost. The time to reach this level was marked. After this point, the shaping capability of the composite was limited. The self-supporting test was carried out at two different temperature surroundings (skin and ambient) as presented in surface temperature test.

In the partly isolated test setup (carpet), the pliability was lost after 5 minutes. After this point the test specimen remained partly flexible for additional 5 minutes followed by final hardening during one hour.

In the skin test setup (thigh), the pliability was lost after 3 minutes. After this point the test specimen remained partly flexible for additional 5 minutes followed by final hardening during half an hour.

After 15 minutes of cooling, the composite gained reasonable load bearing capability (80-90% of the maximum value). At this point no change to the shape of the composite was possible to carry out.

The composite having surface temperature of ~65° C. neither caused any unpleasant feeling for the patient nor caused any skin changes (itching burns etc.).

At a manipulation temperature of 50 to 70° C., typically about +65° C. or slightly more, the splinting material can be manipulated and manually shaped for up to 10 minutes and it is typically pliable for 3-10 minutes after the finishing of heating, depending of the size of splint. The material hardens entirely in one hour. Operation time of the melt material can be expanded by heating the material close to +100° C., which is the temperature limit for the material to be handled without protective gloves. Due to good insulation property of the splinting system, which is based on unique wood-thermoplastic composite, the surface of the splint does not feel burning hot even close to 100° C. The material can be heated up to +150° C. and held there for several hours without changes in the material properties.

It is a unique property of present invention that the surface temperature of splinting system decreases rapidly below its physical hardening temperature of ~55° C. (in less than a minute) and the splinting material still remains pliable down to temperature of 40° C. Cooling time to solidification temperature typically takes 3-5 minutes. This is obviously an advantageous phenomenon when high temperatures close to skin must be avoided during the application.

To achieve rapid solidification of the material, a cooling spray or a cooling gel or wrap can be used.

When the initial post-fracture edema or swelling goes down, our composite cast can be reheated and reshaped and even cut to match new anatomical contour of the fractured limb.

The composite material of the present invention has specific properties which are not present in the existing materials. The uniqueness of the material is based both on the utilized polycaprolactone polymer and the specific sized wood chips.

Figure 13:
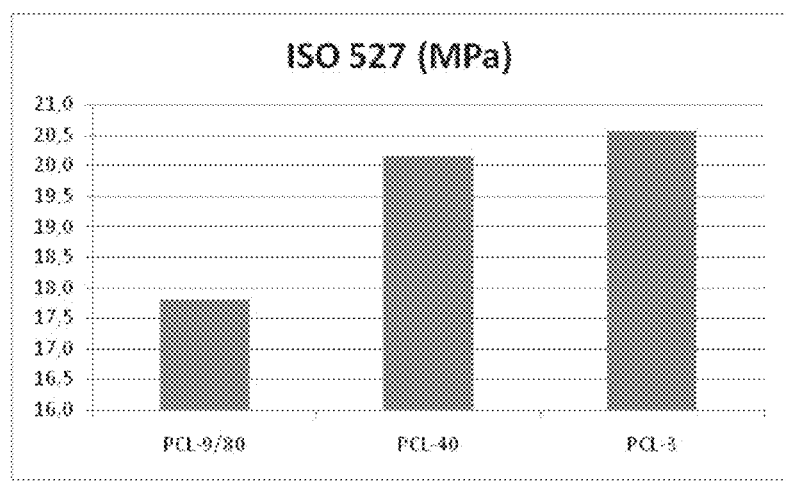
FIG. 13. Mechanical strength (flexural strength) in MPa as according to ISO standard 527. PCL polymers: PCL-9/80 (melt flow index at 80 deg C.), PCL-40 and PCL-3.

For the thermoplastic polymers, Melt Flow Index (MFI) is often used to indicate the process-ability of polymer or the blend of polymers. Molecular weight and degree of chain branching influence a polymer's MFI. Typically, mechanical properties at room temperature are not influenced dramatically by polymer's MFI. This is seen in the FIG. 13, showing the flexural strength of different polycaprolactone polymers.

For the applicability and final properties of splinting system, the properties of compounded polymer at molten stage are more relevant than the flexural strength of pure polymer at room temperature.

Figure 9:
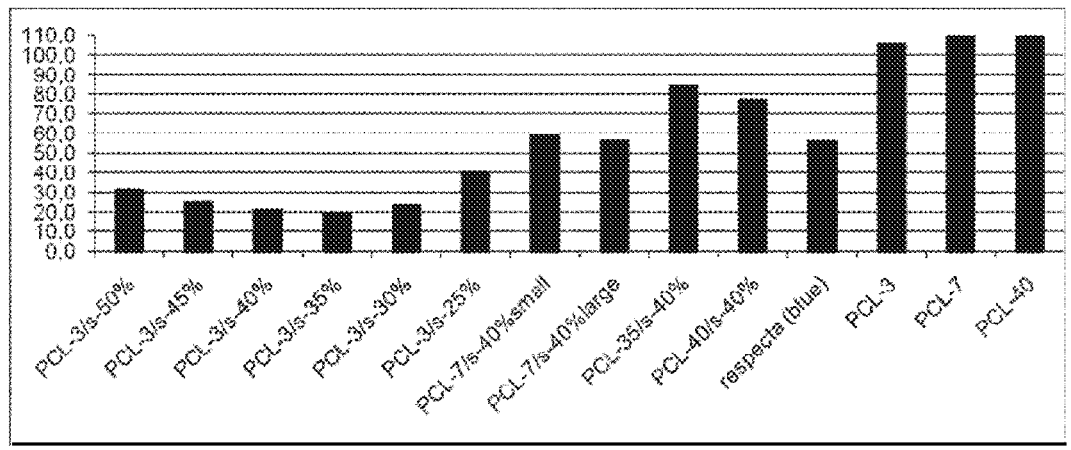
FIG. 9 is a bar chart showing the results of a puncture test (Example 7).
Figure 10:
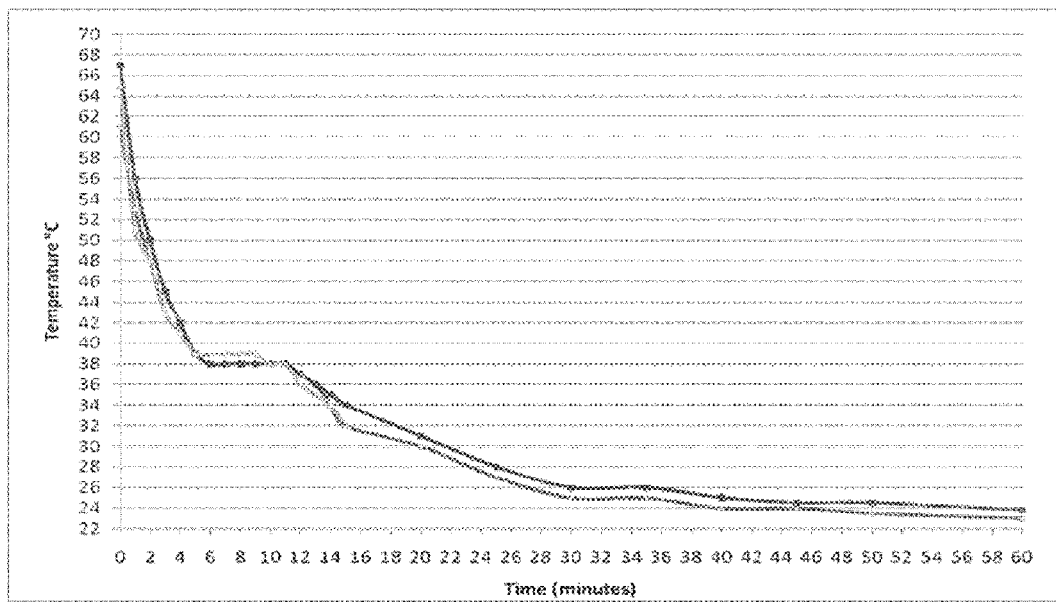
FIG. 10 shows the cooling behavior of the composite splint when positioned onto the isolating carpet (Example 8).
Figure 11:
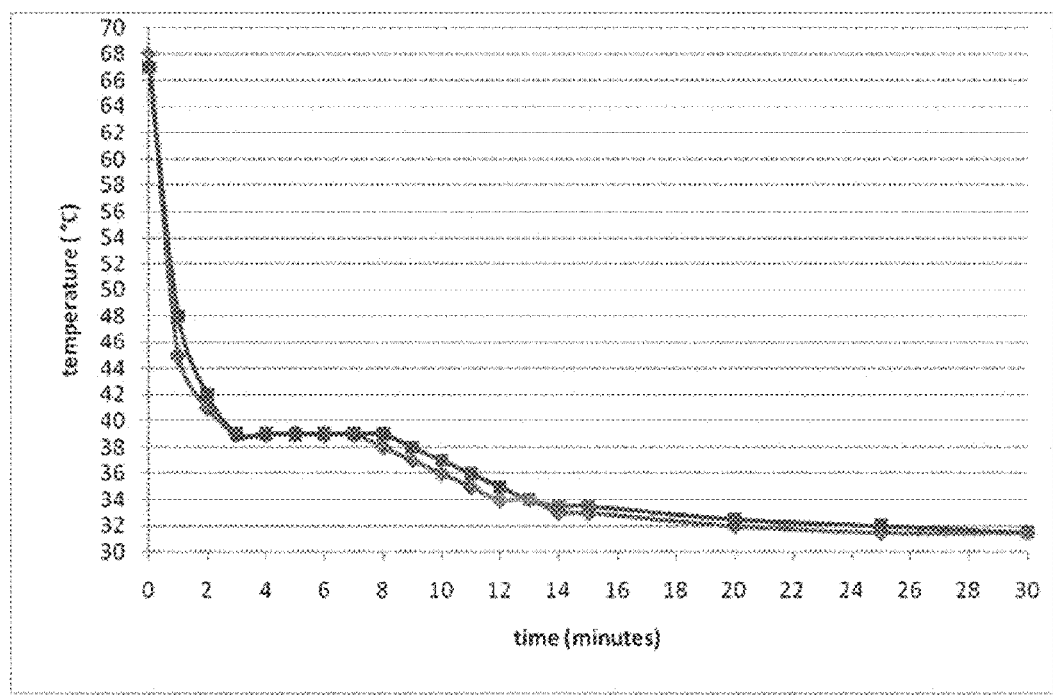
FIG. 11 shows the cooling behavior of the composite splint when positioned onto the isolating carpet (Example 8).

To show uniqueness of splinting application of the present invention, a punctuation test was carried out and the results are shown in FIG. 9. The goal of punctuation test is to gain information about compressive strength of the molten WPC-splint at applicable temperature. The uniqueness of the contouring possibilities of the herein introduced WPC-material can be adequately demonstrated by measuring viscosity of WPC-material at the applicable temperature of ~65° C. with universal penetrometer which is routinely used in determinations of consistency of semi-solid to solid materials such as greases, waxes, cosmetics etc.

The measurements were carried out according to the modified standard D 1321, D 1988 or EN-1426 (Standard Test Method for needle penetration of petroleum waxes and bitumen). At 65° C. carried out measurements reveal useful information about compression strength of the polycaprolactone homopolymer as well as from WPC-material in molten state. The penetration depth of the 100 g needle assembly reflects well on the behavior of the WPC splint during application.

The composites based on PCL having MFI value of 40 are typically very sticky and they do not tolerate any compression without strong rupturing at temperature of 65° C. These composites are not suitable to be used as splints in fracture fixation. The composite based on PCL having MFI value of 7 (CAPA 656) is only slightly sticky, as presented in patent application IE 050593, but during applying it onto limb it does not tolerate strong bending or strong compression without tearing or forming of a dent. Furthermore, PCL-7 possesses no resistance against needle assembly penetration. Even at temperature of 58° C., the needle assembly penetration depth during one second is out of scale (needle reach the bottom of foil cup). Estimated penetration value for PCL-40 was over 1000.

PCL-7 and PCL-3 having MFI value of 7 and 3 respectively are more viscous polymers and their penetrations depths were measured in standard circumstances. The penetration value for PCL-7 was 240 and for PCL-3 the corresponding value was 103 as seen in the FIG. 9.

Materials having a penetration value of 100 reflects well on the material which can be easily mounted onto the fractured limb, but does not tolerate any compression during installation without creeping or wrinkle formation. The composites consisting of polycaprolactone PCL-7, PCL-35 and PCL-40 have MFI values of seven or above, revealed average penetration values between 56 and 88. Worth of mentioning is that commercial splinting material Aquaplast® (respecta blue) revealed penetration value of 55. These composites tolerate moderate compression and could be, in theory, used in splinting applications. Unfortunately the risk of tearing and dent formation under pressure or during bending is too high for medical applications. In addition, the stickiness of these composites may cause undesired fastening to the materials used in fracture fixation operation rooms.

The composite materials of our invention reveal average penetration values between 15 and 50. The value is depending on the wood weight percentage in the composite. The more there is wood the less is the value. When the wood content in the composite is kept between 15 and 50 weight percentage, composites tolerate appropriate compression during mounting and tearing and dent formation during applying can be avoided. Worth of mentioning is that by placing the needle assembly directly onto the wood chip surface, lower penetration value than expected is achieved.

The adhesive properties of composite can be varied by introducing different proportion of wood into the material. This phenomenon can be exploited in production of different kind of splinting applications. Reasonable adhesion is required in all casting/splinting applications. The adhesion forces of the herein introduced composites were tested in a peel adhesion test. The goal of the peel adhesion test is to find appropriate composition for the wood-plastic composite featuring elevated adhesive forces when applied with various gauze bandages. Appropriate adhesion between the splint and the bandage improves the stability of the fracture fixation system. The peeling force should be at such a level that gauze bandage is easy-to-peel with bare hands and without causing unnecessary pain to the patient.

According to the standard SFS-EN 1939 carried out test the adhesive/tape is rolled with 2 kg cylinder shaped roller on substrate. However, in our system roller can't be used due it can form irregularities on the surface of the substrate. Therefore roller was replaced with rectangular shaped steel slab weighting 3.3 kg. By this way the reproducibility of the test reproducibility improved remarkably. The steel slab addresses pressure of 0.09 bars to the gauze which correspond to a gentle press with palm.

The peeling experiments were initiated with the virgin polycaprolactone polymers having high molar mass values along with high melt flow index (MFI) values of 3 (PCL-3) and 7 (PCL-7) g/10 minutes with 2.16 kg standard die at 160° C. The virgin polymers having MFI values 35 and 40 were not suitable for peel testing due they flow at temperature of 65° C. PCL-7 was not suitable for the peeling test. During pressing process the gauze sunk in to the PCL-7 substrate and in addition no peeling was observed when pull-out force reached 193 N. It is obvious that gauze can't be removed of the splint without cutting.

The PCL-3 revealed only insignificant deformation during the pressing process and the test was possible to carry out without problems. The average peeling force value of 19 N was achieved.

The composites having wood weight percentage less than 35 revealed peeling forces above 3 N which is the applicable limit for adhesive forces between gauze and splint. PCL-3/s-30% revealed peeling forces above 20 N. It seems that in this composite ratio of wood and polymer the surface of composite is ideal for the gauze to form relatively strong bond with composite. On the other hand, composite consisting of PCL-7 and wood particles size of 0-0.8 mm (PCL-7/s-40% small), similar to the material presented in the patent WO94/03211, revealed practically zero peeling forces. The small wood particles/fibers at higher content in the composite are evidently not useful when adhesion between bandage material and splint is required.

Self-adhesive forces are usually needed in casting/splinting applications. For example immobilization of fractured foot can be nicely carried out with splint having strongly self-adhesive straps which decrease the possibility of failure of the splint assembly. In some cases when fractured limb is immobilized with circumferentially casting applications it is beneficial if the support can be taken off easily and set again. With our material both the weak and the strong adhesion can be achieved.

Composites containing wood less than 30 weight-% revealed adhesive forces close to 400 N and the composites containing wood over 40 weight-% revealed adhesive forces below 10 N when pressure of ~0.1 bar was used (correspond to a gentle press with palm). The former having adhesion forces above 100 N can be considered to be "everlasting" bond which can't be broken without casting saw. The latter composites having adhesion forces less than 10 N can be easily separated apart by hands.

As disclosed above, the novel composite material of the present invention has a composition and properties that are substantially well suited for use in orthopedic situations.

Generally, the composite material can be used to form an exo-skeletal device on a portion of an animals or human beings body or body part. The exo-skeletal device can be used as a shin-pad, wrist guard or even a foot bed for footwear. However, it is especially well suited as a splint or cast structure to immobilize, or partially immobilize a portion of an animals or humans body or body part.

Method of Using the Composite Material

The composite material of the present invention is manufactured in to either a blank or in to a desired, specific shape or form. Ideally, the blanks and forms are linier, two dimensional and easily stackable. The blanks can be either substantially larger than the intended size to be applied to the animal or human being, herein referred to as the patient, or of substantially similar size.

In the instance when the blank is of a large size than desired, the blank can be cut with normal scissors or other conventional cutting means before application. Such a large blank is preferable in the sense that one blank may be cut in to several splints at various times according to the size required by each. Therefore, it is not necessary to store many different shapes and sizes of the material, which take up room and may be rarely used. Additionally, multiple splints may be cut from one blank in such a way as to maximize the material used and not produce a large amount of waste product.

Once the proper size and shaped piece of material is obtained, cut or selected, the material is then heated to the desired operating temperature by a heating means. Numerous heating means are known in the art, but it is preferable to uniformly heat the material to a specific desired temperature. If the temperature is too high then there is risk of discomfort or harm to the patient's skin. If the temperature is not high enough then the material will not be able to properly conform to the patient's body.

Therefore, in one embodiment, the composite materials are provided along with a heater which is specifically tailored to the application of the composite materials. The heater may have an adjustable thermostat or may be pre-programmed to heat automatically to the desired temperature. Ideally, the heater will have a heating element capable of heating an entire blank or form of the composite material evenly and completely. The size of the heater should be sufficient enough to handle the size of the composite materials to be used. The heater may be given complimentary along with complementary or paid composite material blanks or forms to entice people to use the system and material.

In cases where the heating element is other than one specifically tailored to the present composite material it can be selected from the range of known heating elements including contact heaters, convection heaters, chemical heating and the like.

Once the composite material blank or form is heated to the desired temperature, as discussed above, then the material can be placed on the patient in the desired location to form the exo-skeletal device. The advantage of the present material is that it can be handled by hand without any protective requirement such as gloves. Equally important is that the material can be formed directly against the patient's skin. However, it can be advantageous to have some material, such as gauze or other cloth/cloth like material, directly in contact with the patients skin and to form the composite material over that material.

With the composite material still pliable and moldable, it can be fit to contour the patient's body part nearly or exactly. Additionally, if the initial placement is not desirable, the material can be moved while still moldable to a more desirable location. If the material has lost its desired moldability, then it can be reheated and likewise moved to the new location. One of the particular advantages of the present material is that it can be heated and cooled many times without degrading its mechanical properties.

When the composite material is located properly and molded to the desired form, then it can be allowed to cool to a temperature where it can be removed but maintain its shape. The cooling may be accomplished by allowing the ambient conditions to reduce the temperature of the material or the cooling may be aided by spraying the material with water or another chemical to speed up the cooling. Additionally, solid cooling means can be used to cool the material such as a cold pack or ice place directly against the composite material.

If the final device is intended to remain attached to the specific body portion or part, a fastening means can be employed to attach the device to the body part. In the case of a splint, gauze can be wrapped around the splint and body part. The adhesive properties of the not yet cooled composite material will hold the gauze in place, therefore facilitating the immobilization of the intended body part. Other fastening means apart from gauze may also be attached as desirable or necessary.

Once the device is cooled to or near room temperature, with or without the fastening means, then it will remain substantially rigid until the time at which it is reheated. In the case of a splint or cast, the device need not be removed for medical imaging such as x-rays. However, if the splint or cast was originally place while there was swelling present, it can be easily heated and reformed to better fit the unswelled shape of the body part. In this sense, less material is wasted since in previous splinting devices a completely new splint/cast would be required.

When the device is no longer needed for its previous purpose it can be reheated, removed if necessary, and either flattened or stored as is until the next time when it is required. The resultant material has the same mechanical properties in subsequent uses as in previous uses and is therefore not degraded through multiple uses. However, when the composite material is desired to be discarded, it is biodegradable and therefore ecologically friendly.

As mentioned above, and as will be discussed below in connection with the examples, the present composition can be used as a composite material for use as an orthopedic material. Such materials are exemplified by finger splints, shown in FIG. 4, wrist casts, shown in FIGS. 5-7, and ankle casts. Generally, the platy particles form about 30 to 70%, preferably in excess of 40 up to about 60%, of the total weight of the composition, for finger splints and for ankle casts about 20 to 60%, preferably about 30 to 50% of the total weight of the composition. There is typically a greater portion of the larger particles present in the larger casts which will reduce the total weight of the cast without impairing the strength properties thereof.

The following non-limiting examples illustrate the invention.

In all the below presented examples, the polycaprolactone polymer used was a commercially available PCL homopolymer supplied under the tradename CAPA 6800 by Perstorp Ltd., Sweden). The polycaprolactone has a melt flow rate of about 3 g/10 min (measured at 150° C. and with a weight of 2.16 kg) and referred to as "PCL-3". As mentioned above, another caprolactone homopolymer also used had a significantly higher melt flow rate of about 7 g/10 min (referred to as "PCL-7").

The wood material, if not separately indicated, was conventional spruce chips produced at a Finnish saw mill. In some of the examples wood particles of other wood species were used. The chips, in particular the spruce chips, were occasionally used in the form of a fraction sieved to an average size of 1-2.5 mm.

EXAMPLE 1

The influence of the reinforcing component on mechanical properties was studied with the 3-point bending test. The flexural strengths and modulus of the composites were measured with universal testing machine Instron 4411. A neat PCL, without any reinforcement, was used as control.

The test samples (dimensions 55×10.5×5.5 mm) were prepared by mixing constant ratio of different size wood chips (30 weight %) and epsilon-polycaprolactone homopolymer (70 weight %) and pressed into a Teflon mould. The melting and shaping of samples until a homogenous distribution of components was achieved. The samples were tested by constant cross head speed of 10 mm/min. The 3-point bending forces are presented graphically in FIG. 1 and Specific Young's modulus of elasticity in FIG. 2.

In FIG. 1 the reinforcing effect of wood particles to the flexural strength of composites can be clearly observed.

Figure 2:
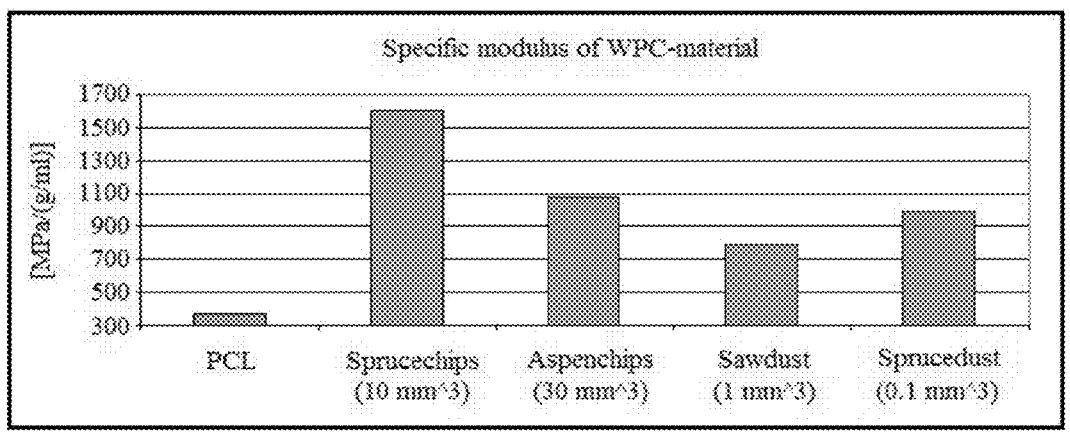
FIG. 2 is a graphical representation of the specific modulus (E/p) of test sample in 3-point bending test (PCL quality=PCL-3).

With the neat polymer PCL (CAPA 6800) the stress at yield is 19 MPa but after incorporating 30 weight-% of different sized wood particles to the polymer stress values increased over 20% reaching value of ~27 MPa at the best. The difference in specific modulus values of pure PCL and herein introduced composites were even greater (FIG. 2). Pure PCL revealed specific modulus value of ~400 MPa and corresponding value with the composite reinforced with wood, particles having average volume of 10 mm$^3$, was slightly over 1500 MPa. In the worst case when composite was reinforced with small wood particles modulus values were still two times greater than with pure PCL homopolymer.

EXAMPLE 2

Figure 3:
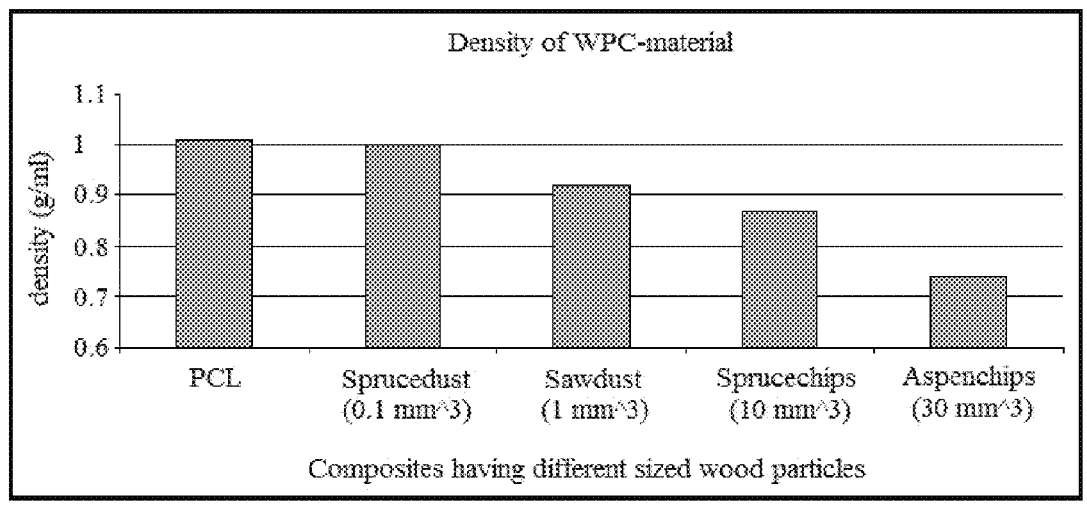
FIG. 3 shows the densities of composites having different sized wood particles. (PCL quality=PCL-3).

The densities of the samples prepared in Example 1 for mechanical testing were measured by determining the dimensions of the regular size samples and weighting them. The densities of the composites are graphically presented in FIG. 3. As will appear, composites according to the present invention have a considerably smaller density than polycaprolactone as such and are therefore suitable for lightweight splinting applications.

As mentioned above, in WO 94/03211 a composite material is described, based upon polycaprolactone, ground almond shell and wood flour. The known material is impaired by several disadvantages, such as a high density of 1.1 kg/dm$^3$ or even more, as a result of the small particle sizes of the filler material [wood, less than 600 microns (600 μm)].

EXAMPLE 3

The composite material prepared in the Example 3 was tooled into a plate suitable for making a splint cast to support finger (a "finger splint").

Approximately 5 grams of composite material was cast to a plate at 100° C. and allowed to cool down. The composite was re-heated up to 70° C. and when still warm and moldable (above 65° C.) the cast composite was manipulated with the help of roller pin to form of a plate, thickness approximately 2 mm. The size of received composite plate was 35×60 mm.

Figure 4:
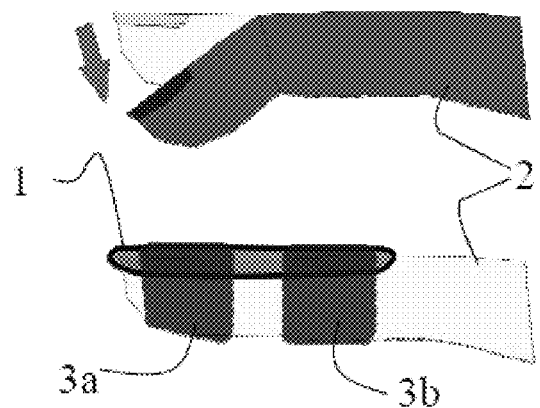
FIG. 4 shows in a schematic side-view the use of the present material as a cast for treating ruptures of the extensor tendon in a the first finger joint; (example 3)

FIG. 4 shows the use of the finger splint. The upper drawing illustrates an injured (mallet) index finger 2 which has a rupture of the extensor cordon. As will appear, the composite plate 1 can be applied directly on the dorsal side of the mallet finger 2. The composite plate can shaped to contour the finger so that the palmar side of finger is left open. Upon cooling the composite splint solidifies. Cooling was accelerated with a wet tissue. After cooling, ordinary bandage (strips 3a and 3b) can be added to immobilize the treated finger.

When removing the composite cast 1, a smooth surface inside the splint is observed having no wrinkles or other irregular shapes causing irritation of skin.

EXAMPLE 4

Figure 5:
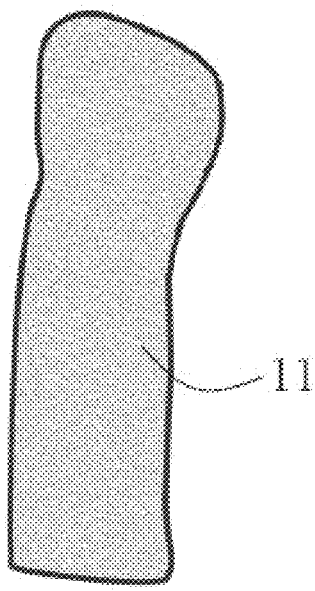
FIG. 5 shows a schematic fashion a front-view of a reshapable wrist cast; (example 4)

This example describes the production of a re-shapable wrist cast 11 having the general shape shown in FIG. 5.

Approximately 100 grams of composite material prepared in Example 1 was cast onto a metal plate and release paper at 100° C. and allowed to cool down. The composite was re-heated up to 70° C. and when still warm and moldable the cast composite was manipulated to form of a thick plate, thickness approximately 6 mm. Excess of materials was cut away with scissors when still warm. The cut edges were gently contoured by hand in order to soften the sharp edges. The size of received composite plate was 12×25 cm.

The composite plate was applied directly on repositioned wrist. The composite plate was left open on medial side of wrist. The wrist was kept repositioned until the cast had solidified.

The semi-open wrist cast can be easily removed and re-shaped if after imaging the clinician need to the repair the resulted repositioning of wrist bones. The wrist cast may be re-softened at the oven heated to 70° C. or in water bath and replaced in the corrected position on the wrist.

EXAMPLE 5

This example illustrates the preparation of an anatomic ankle cast and the application thereof.

200 grams of composite material manufactured in the Example 2 was cast on release paper at 100° C. and allowed to cool down. The composite was re-heated up to 70° C. in heat oven to resemble a thick plate, thickness approximately 8 mm. The received composite plate, dimensions 15×40 cm was cut to anatomical shape with scissors when it was still warm. Especially area that is needed for the medical personnel to hold the leg when repositioning the ankle was cut slightly open. Also, extra strips were cut to be later attached on the anterior side of the cast. The cut edges were gently contoured by hand in order to soften the sharp edges.

Figure 6:
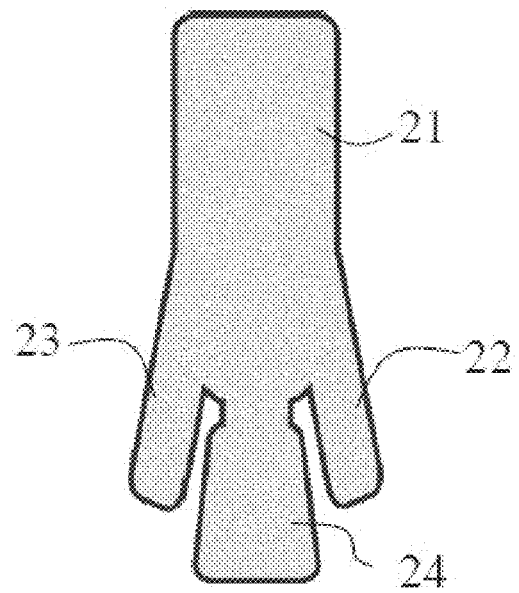
FIG. 6 shows in a schematic fashion a front-view of an anatomic ankle cast according to an embodiment of the invention; (example 5)

FIG. 6 shows the general form of the produced cast plate. Reference numeral 21 refers to the cast plate and numerals 22 to 24 to foldable flaps.

FIGS. 7a and 7b show how the composite plate 21 can be reshaped when applied directly on the leg during repositioning of the ankle after an injury.

Thus, in the application, the leg is kept repositioned until the cast has solidified. When still warm, the cut flaps 22 and 23 are folded along folding lines 25 and 26 and compressed gently on the anterior side of the composite cast. The cut flap 24 can in a similar fashion be bent and shaped by folding its side portions along folding lines 27 and 28. The material is non-tack but it grips well with itself when it is still moldable, i.e. above 65° C.

EXAMPLE 6

This example illustrates how a test according to the peel adhesion test method shows the relative bond strength of a given tape/bandage to surface (material and texture) of composite splint. A molten WPC-material can be considered to be a pressure sensitive adhesive. In this test gauze bandage is pressed with steel slab surface of molten composite for 30 seconds and allowed to cool to RT. After hardening of the composite gauze is peeled off at a 180° angle from substrate at a constant peel rate by using Instron mechanical testing device. The measurements were carried out according to the modified standard SFS-EN 1939 (Standard Test Method for Peel Adhesion of Pressure-Sensitive Tape).

A composite plate (width·length·thickness=60 mm·~90 mm·~3.5 mm) was placed into oven and allowed to set at a temperature of 65° C. during 30 minutes. After heating procedure the composite plate was removed from the oven followed by pressing a strip of elastic gauze bandage (width 50 mm, length ~250 mm, thickness 0.6 mm) to composite plate using a 3.3 kg weight (0.09 bar). The gauze is folded twice on the composite plate so that area size of w·l=60 mm·20 mm·3.1 mm) is free. After 30 seconds of pressing the slab is removed and the composite/gauze assembly was allowed cool down to room temperature. After cooling the system was placed into Instron testing machine. The loose end of the strip was connected to the peel arm and the composite plate was mounted horizontally onto a stage allowing ~180° angle to be maintained as the tape was pulled from the surface of the composite (FIG. 8). The rate of peeling was kept constant at 50 mm/min. The peeling force as a function of distance was collected. The peeling is ended before the last 20 mm of the test specimen is achieved.

As can be seen in FIG. 8 the composite manufactured of PCL-7 and small wood particles in weight ratio of 60:40 (particle size between 0-0.8 mm) revealed zero adhesive force (material has similar properties with the material presented in patent WO 94/03211). After changing the wood particles to larger ones (particle size between 1 mm-5 mm) an adhesion force in the range of 1 to 50 N was detected. This force is sufficient for adhering the bandages to the surface to avoid sliding of them when applying the splint on a patient. When the large wood particles were combined with high molar mass polycaprolactone in weight ratio of 70:30 adhesion force of 23 N was achieved.

The size of the wood particles in the composites containing over 40 weight-% of wood has dramatic influence to the adhering properties of the composite. For example composite consisting of 40 weight-% of wood dust and 60 weight-% of CAPA 6500 possesses extremely smooth surface, chipboard-like, without any adhering properties. After changing the wood particles with larger ones minor adhesion was observed being enough for holding the bandage material stationary during the circumferential casting procedure.

It should be pointed out that PCL-7 as such had an adhesive force of 197 N. The adhesion is very strong and the gauge bandage cannot be anymore removed by hands from the polymer sample.

EXAMPLE 7

A volume of material is softened to operating temperature of 65° C. in foil container beaker (depth of at least 15 mm in excess of the expected penetration). The beaker is placed on the stand of the penetration apparatus (FIG. 9) "remove" and the needle is adjusted to make contact with the surface of the sample. The dial reading is adjusted to zero and the needle is released for exactly 5 seconds. The dial reading is recorded. The procedure is repeated three times.

Penetration is read from indicator dial of 0-400 divisions each representing 0.1 mm of penetration. The materials presented in the figures are PCL-3 (polycaprolactone homopolymer having MFI of 3 g/10 min/2.16 kg/die 160° C.); PCL-40 (polycaprolactone homopolymer having MFI of 40 g/10 min/2.16 kg/die 160° C.); PCL-3/s-40% (composite consisting of polycaprolactone MFI=3 and spruce chips 40 weight percentage); PCL-3/s-50% (composite consisting of polycaprolactone MFI=3 and spruce chips 50 weight percentage).

FIG. 9 shows the needle penetration depths into PCL homopolymers and wood-plastic composites. Experiments are carried out with the universal manual penetrometer.

The examples and specific embodiments are not meant to limit the present invention. One of ordinary skill in the art will recognize uses and modifications of the composite material presented herein that do not depart from the scope of the invention. Specifically, it is conceivable to add additional layers to the composite material, such as a fabric layer to be in direct contact with the patients skin for comfort or a layer containing a chemical composition that when activated automatically heats the composite material to a moldable state, therefore no longer requiring a separate heating means.

The composite materials of our invention reveal average penetration values between 15 and 50. The value is depending on the wood weight percentage in the composite. The more there is wood the less is the value. When the wood content in the composite is kept between 15 and 50 weight percentage, composites tolerate appropriate compression during mounting and tearing and dent formation during applying can be avoided.

EXAMPLE 8

Surface temperature test reveals basic information of the composite surface temperature after heating procedure of the test specimen in the oven has been ended. To simulate cooling process of the composite plate in real applying situation test specimen was heated to 65° C. and placed directly on the skin of the thigh and allowed to reach the equilibrium temperature. The cooling of the plate was followed with IR thermometer pistol. Similar test was also carried out by placing the heated test specimen onto the material having low thermal conductivity (Astro Turf®) carpet) which was positioned onto the office table at ambient temperature (22° C.) and allowed to reach the equilibrium temperature.

The composite test specimen (10 cm*40 cm*4 mm) was placed into in-house developed heating device and heated to 65° C. After heating procedure sample was removed from the oven and positioned either onto the skin of the thigh or onto the carpet (Astro Turf®) covered with baking paper. The temperature of the cooling composite splint surface was followed with IR thermometer pistol (Tamo Distance Thermo).

The cooling of the present composite splint when placed onto the carpet having low thermal conductivity represents the situation when the splint has longest possible time to reach equilibrium temperature at RT. Based on the results the cooling process can be divided into three phases. 1) Rapid cooling phase when the temperature of test sample decreases from starting temperature of ~65° C. to 38° C. during 5 minutes. 2) Steady state phase during the temperature of test specimen remains at 38° C. for 5 minutes. 3) Slow cooling phase during the temperature of the test specimen slowly approaches the equilibrium temperature of surroundings within 50 minutes.

The cooling of the present composite splint when placed directly onto the skin of the thigh represents the situation when the splint has shortest possible time to reach equilibrium temperature at limb temperature of ~31° C. when no additional cooling is utilized (e.g. cooling spray). In general, the temperature behavior of the test specimen was similar with data presented in the previous experiment. The only differences being the faster rapid cooling phase and Slow cooling phase. The temperature of the test specimen decreases from ~67° C. to 38° C. during 3 minutes. 2) Steady state phase at 39° C. lasts for 5 minutes. 3) Slow cooling phase during the temperature of the test specimen slowly approaches the equilibrium temperature of surroundings during 30 minutes.

EXAMPLE 9

Self-supporting/full hardening test reveals information of the changes in pliability of the composite test specimen while cooling it down from 65° C. to the equilibrium temperature. The pliability of the test specimen was tested manually by lifting one side of sample and allowing it to settle down. After the settling procedure of the sample plate is not anymore complete the pliability is lost. The time to reach this level will be marked. After this point, the shaping capability of the composite will be limited. The self-supporting test will be carried out at two different temperature surroundings (skin and ambient) as presented in surface temperature test. In the isolated test setup (carpet), the pliability was lost after 5 minutes. After this point the test specimen remained partly flexible for 5 minutes followed by final hardening during one hour. In the skin test setup (thigh), the pliability was lost after 3 minutes. After this point the test specimen remained partly flexible for 5 minutes followed by final hardening during half an hour. After 15 minutes of cooling the composite splint gained reasonable load bearing capability of 80-90% of the maximum value). At this point no changes to the shape of the composite splint can be carried out.

EXAMPLE 10

Figure 12:
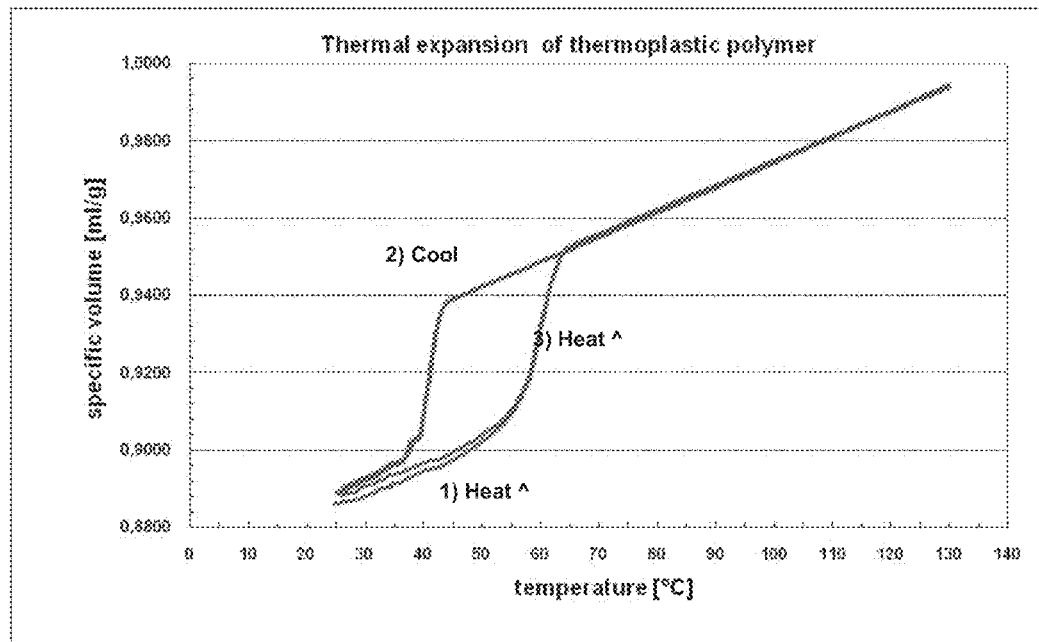
FIG. 12. Thermal expansion behaviour of crystalline thermoplastic polymer. "Undercooling" effect is observed when the polymer is cooled down. The polymer melts at 65 deg C. and solidifies approximately at 40 degrees of Celsius.

An analysis of volumetric change of polymer was carried out for the thermoplastic polymer utilized in the Example 1. As it is seen from the thermal expansion curves (FIG. 12), the undercooling effect of the polymer is responsible for the desired shapability of a heated splinting system down to temperature 40 deg C. The re-shapability of the polymer is returned only after heating the polymer again to 65 deg C.

The invention claimed is:

1. A method for forming a removable exo-skeletal device on a portion of a body of a human or animal, the method comprising the steps of;
shaping a composite material to a desired linear form,
heating the linearly shaped composite material in a heating device to a temperature high enough to soften the composite material yet not so high as to be harmful to skin of the human or animal,
arranging the softened composite material on a desired portion of the body of the human or animal so that it conforms to a desired three-dimensional contoured exo-skeletal shape,
cooling the contoured exo-skeletal composite material to a temperature approximating an ambient temperature such that the contoured exo-skeletal composite material resumes a same rigidity as the shaped linear composite material prior to heating,
wherein the composite material is formed from a homogenous mixture of a first and second component,
the first component comprising a thermoplastic polymer selected from the group of biodegradable polymers and mixtures thereof, and
the second component comprising platy wood particles in which a ratio of a thickness of the platy wood particles to the smaller of a width or a length of the platy wood particles is between 1:2 and 1:500.

2. The method according to claim 1, wherein the composite material is manufactured at a first point in time, the composite material is shaped to a desired linear form at a second point in time, and the linearly shaped heated composite material is applied to the desired exo-skeletal shape at a third point in time, the second point in time being substantially closer to the third point in time than to the first point in time, such that the linear formation of the composite material is considered part of an applying process of the composite material to the desired portion of the body.

3. The method according to claim 2, wherein the composite material is shaped to a desired linear form by manually cutting the composite material.

4. The method according to claim 1, wherein the composite material is manufactured at a first point in time, the composite material is shaped to a desired linear form at a second point in time, and the linearly shaped heated composite material is contoured to the desired exo-skeletal shape at a third point in time, the second point in time being substantially closer to the first point in time than to the third point in time, such that the linear formation of the composite material is considered part of the manufacturing process of the composite material.

5. The method according to claim 1, wherein the composite material is shaped to a desired linear form during manufacture by a process selected from laser cutting, water cutting, mechanical cutting, stamping and extrusion.

6. The method according to claim 1, comprising the additional step prior to cooling the heated composite material of:
securing the exo-skeletal device to an intended portion of the body by means of the adhesive properties of the heated composite material.

7. The method according to claim 1, wherein the wood particles greater in size than powder are granular or platy and make up more than 70% of the woody material, said woody material making up more than 70% of the second component.

8. The method according to claim 1, wherein said woody material is comprised substantially of granular particles having a cubic shape with dimensions greater than 0.6 mm and up to 3.0 mm.

9. The method according to claim 1, wherein the method is used for immobilizing the desired portion of the body.

10. The method according to claim 1, wherein;
the wood particles correspond to platy wood particles, and
a thickness of the platy wood particles is grater than 0.1 mm.

11. The method according to claim 1, wherein the thermoplastic polymer is polycaprolactone polymer having a melt flow index that is less than 7.

12. A method for shaping a composite material to snugly fit against a part of a body of a mammal, comprising:
providing the composite material in a form of an essentially planar blank having a first component formed by a polymer and a second component formed by a reinforcing material, wherein
the first component comprises a thermoplastic polymer selected from the group of biodegradable polymers and mixtures thereof, and
the second component comprises platy wood particles in which a ratio of a thickness of the platy wood particles to the smaller of a width or a length of the platy wood particles is between 1:2 and 1:500.
heating the blank to a temperature in a range of 50 to 70 ° C. to convert the composite material into a manually formable state,
applying the material against a target part of the body to make the composite material take up the form of the target part, and
cooling the composite material to a temperature of less than 45 ° C. to make the composite material rigid.

13. The method according to claim 12, wherein the blank is cooled actively with the help of a cold blanket, cold spray or by gentle air boost, or other method enhancing a heat transfer from a surface of the blank.

14. The method according to claim 13, wherein the cooling of the contoured exo-skeletal device is achieved by one of more of the following, allowing ambient conditions to lower the temperature of the device, spraying the device with a liquid or a gas at a temperature lower than the device, or placing a solid mass adjacent to the device which is at a lower temperature than an ambient temperature.

15. The method according to claim 12, wherein the blank is heated in a contact-type heater, non-contact heater, oven or infra red (IR) heater.

16. The method according to claim 12, wherein the blank is cut into form before heating.

17. The method according to claim 12, wherein a thickness of the platy wood particles is greater than 0.1 mm.

18. The method according to claim 12, wherein the thermoplastic polymer is polycaprolactone polymer having a melt flow index that is less than 7.

\* \* \* \* \*